US010881779B2

(12) United States Patent
Suffritti et al.

(10) Patent No.: US 10,881,779 B2
(45) Date of Patent: *Jan. 5, 2021

(54) APPARATUS FOR EXTRACORPOREAL BLOOD TREATMENT

(71) Applicant: GAMBRO LUNDIA AB, Lund (SE)

(72) Inventors: Mauro Suffritti, Medolla (IT); Michela Carpani, San Biagio-San Felice sul Panaro (IT)

(73) Assignee: Gambro Lundia AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/448,128

(22) Filed: Jun. 21, 2019

(65) Prior Publication Data

US 2019/0298907 A1 Oct. 3, 2019

Related U.S. Application Data

(63) Continuation of application No. 15/353,883, filed on Nov. 17, 2016, now Pat. No. 10,342,911, which is a
(Continued)

(30) Foreign Application Priority Data

Sep. 30, 2010 (EP) .................................... 10012243

(51) Int. Cl.
*A61M 1/34* (2006.01)
*B01D 61/22* (2006.01)
(Continued)

(52) U.S. Cl.
CPC .......... *A61M 1/341* (2014.02); *A61M 1/1603* (2014.02); *A61M 1/1615* (2014.02);
(Continued)

(58) Field of Classification Search
CPC .. A61M 1/341; A61M 1/3437; A61M 1/3434; A61M 1/3441; A61M 2205/502;
(Continued)

(56) References Cited

U.S. PATENT DOCUMENTS 4,711,715 A 12/1987 Polaschegg
4,753,733 A 6/1988 Ramstack
(Continued)

FOREIGN PATENT DOCUMENTS

| CN | 101010110 | 4/2011 |
|----|-----------|--------|
| FR | 2 852 515 | 9/2004 |
| WO | WO 2006/011009 | 2/2006 |

OTHER PUBLICATIONS

PCT International Search Report and Written Opinion dated Feb. 29, 2012 for PCT/EP2011/002097.

*Primary Examiner* — Joseph W Drodge
(74) *Attorney, Agent, or Firm* — Mueting Raasch Group

(57) ABSTRACT

An apparatus for extracorporeal blood treatment, comprising a treatment unit (2) having a first chamber (3) and a second chamber (4) separated from one another by a semipermeable membrane (5), a blood removal line (6) connected in inlet with the first chamber (3) and a blood return line (7) connected in outlet with the first chamber; an infusion line (9;9a, 9b) of a replacement fluid and a fluid evacuation line (10) connected in outlet from the second chamber. A regulating device (20) of a transmembrane pressure is active on at least one of the lines and a control unit (15) is configured to: command the regulating device (20) by setting a first increase ($\delta TMP_1$), determine a value of a control parameter ($\varphi_1$) corresponding to the first increase, compare the value of the control parameter ($\varphi_1$) with a reference value ($\varphi_{ref}$) and, if the value of the control parameter is greater than the reference value, command the regulating device (20) by
(Continued)

setting a second increase ($\delta TMP_2$) which is greater than the first increase ($\delta TMP_1$).

20 Claims, 6 Drawing Sheets

Related U.S. Application Data continuation of application No. 13/876,368, filed as application No. PCT/IB2011/002097 on Sep. 8, 2011, now Pat. No. 9,533,087.

(51) Int. Cl.
  *B01D 61/32* (2006.01)
  *A61M 1/36* (2006.01)
  *A61M 1/16* (2006.01)

(52) U.S. Cl.
  CPC ........ *A61M 1/3434* (2014.02); *A61M 1/3437* (2014.02); *A61M 1/3441* (2013.01); *A61M 1/3639* (2013.01); *B01D 61/22* (2013.01); *B01D 61/32* (2013.01); *A61M 2205/3331* (2013.01); *A61M 2205/502* (2013.01); *A61M 2205/52* (2013.01); *B01D 2311/14* (2013.01)

(58) Field of Classification Search
  CPC ...... A61M 2205/52; A61M 2205/3331; A61M 2205/3334; A61M 2205/3341; A61M 2205/3351; A61M 2205/3355; A61M 1/02; A61M 1/024; A61M 1/0281; A61M 1/16; A61M 1/1601; A61M 1/1615; A61M 1/1602; A61M 1/1603; A61M 1/342; A61M 1/3424; A61M 1/3427; A61M 1/3431; A61M 36/3607; A61M 1/3403; A61M 1/3406; A61M 1/3496; A61M 1/36; A61M 1/3607; A61M 1/3639; B01D 61/22; B01D 61/32; B01D 2311/14; B01D 61/20; B01D 61/24; B01D 61/28; B01D 61/30

USPC ........ 210/90, 97, 134, 321.6, 645, 646, 741; 604/4.01, 5.01, 6.01, 6.09, 6.1, 6.11, 19, 604/27, 30

See application file for complete search history.

(56) References Cited

U.S. PATENT DOCUMENTS

| | | | | |
|---|---|---|---|---|
| 4,769,150 | A * | 9/1988 | Ramstack | A61M 1/3496 210/195.2 |
| 4,828,543 | A | 5/1989 | Weiss | |
| 4,923,598 | A | 5/1990 | Schal | |
| 5,053,121 | A * | 10/1991 | Schoendorfer | A61M 1/3403 210/90 |
| 7,291,269 | B2 | 11/2007 | Chevallet | |
| 7,435,235 | B2 | 10/2008 | Stemby | |
| 7,544,296 | B2 | 6/2009 | Kopf | |
| 7,935,258 | B2 | 5/2011 | Rovatti | |
| 8,105,260 | B2 | 1/2012 | Tonelli | |
| 8,246,826 | B2 | 8/2012 | Wilt | |
| 8,647,290 | B2 | 2/2014 | Masala | |
| 8,771,215 | B2 | 7/2014 | Tonelli | |
| 9,199,027 | B2 | 12/2015 | Fontanazzi | |
| 9,220,830 | B2 | 12/2015 | Fontanazzi | |
| 9,533,087 | B2 | 1/2017 | Suffritti | |
| 9,925,321 | B2 | 3/2018 | Surace | |
| 10,342,911 | B2 * | 7/2019 | Suffritti | A61M 1/3441 |
| 2002/0147423 | A1 | 10/2002 | Burbank | |
| 2005/0131331 | A1 | 6/2005 | Kelly | |
| 2007/0278155 | A1 | 12/2007 | Lo | |
| 2008/0015487 | A1 | 1/2008 | Szamosfalvi | |
| 2008/0149551 | A1 | 6/2008 | Brugger | |
| 2008/0215247 | A1 | 9/2008 | Tonelli | |
| 2008/0237128 | A1 | 10/2008 | Rovatti | |
| 2009/0008306 | A1 | 1/2009 | Cicchello | |
| 2009/0152200 | A1 * | 6/2009 | Lannoy | A61M 1/3403 210/647 |
| 2010/0038317 | A1 | 2/2010 | Bissler | |
| 2010/0168925 | A1 | 7/2010 | Hilgers | |
| 2011/0240555 | A1 | 10/2011 | Ficheux | |

* cited by examiner

APPARATUS FOR EXTRACORPOREAL BLOOD TREATMENT

This application is a continuation of U.S. application Ser. No. 15/353,883, filed Nov. 17, 2016, which is a continuation of U.S. application Ser. No. 13/876,368 filed Jul. 30, 2013, now U.S. Pat. No. 9,533,087, which is a U.S. National Stage Application of International Application No. PCT/IB2011/002097 filed Sep. 8, 2011, which was published in English on Apr. 5, 2012 as International Patent Publication WO 2012/042322 A1. International Application No. PCT/IB2011/002097 also claims priority to European Application No. 10012243.1 filed Sep. 30, 2010. A certified copy of European Application No. 10012243.1 filed Sep. 30, 2010, was provided and is available in U.S. patent application Ser. No. 13/876,368.

The present invention relates to an apparatus for extracorporeal blood treatment.

Apparatus for extracorporeal blood treatment comprise at least a treatment unit (for example a dialyser or a filter or ultrafilter or a plasma filter or a filtration unit of other type) having a semipermeable membrane which separates the treatment unit into two chambers. An extracorporeal blood circuit enables circulation of blood removed from a patient internally of the first chamber. At the same time, and typically in an opposite direction to the blood current, a treatment fluid is made to circulate through an appropriate circuit in the second chamber of the treatment unit.

This type of apparatus for blood treatment can be used for removal of solutes and excess fluid from the blood of patients suffering from kidney failure. A particular type of apparatus for blood treatment comprises the presence of an infusion line predisposed to send a replacement fluid into the extracorporeal blood circuit. In this case the treatment apparatus are called apparatus for hemofiltration or hemodiafiltration. The infusion line or lines are connected upstream and/or downstream with respect to the two treatment units.

The above-described blood treatment apparatus can be controlled in various modes.

In a first mode the apparatus can be volumetrically controlled, i.e. such as to have predetermined flow-rates along the various lines of fluid transport.

Alternatively the apparatus can be controlled such that the trans-membrane pressure (called TMP herein below) follows a set value. In this case, one or more pumps act on an evacuation line exiting from the second treatment chamber such as to control the transmembrane pressure TMP. In other words the pumps on the evacuation line are moved such that the transmembrane pressure is constant or follows a given profile. Contemporaneously, a pump acting on the infusion line supplies a replacement fluid at a flow rate which is regulated either with the aim of achieving a user-set weight loss in a predetermined treatment time or, alternatively, with the aim of contemporaneously achieving both a predetermined weight loss and a predetermined infusion volume in a patient.

The treatment units (for example filters, hemofilters, hemodiafilters, etc.) typically used have a characteristic curve which relates the TMP and fluid volume crossing the membrane (ultrafiltration volume); this curve exhibits a zone in which to the TMP increase there is a more or less proportional increase in volume of ultrafiltered fluid across the membrane, followed by a zone in which the growth of ultrafiltration volume drops up to reaching a plateau where there is no significant increase in ultrafiltration on increase of the TMP. In this situation, application no. WO2005IB01482 illustrates an apparatus and a process for setting the value of the TMP to a level which is such as to maximise the ultrafiltration flow and, consequently, the fluid of infused fluid into the patient. This solution is advantageous since by maximising the ultrafiltration and infusion flow rate, the convective exchange through the membrane is maximised and thus so is the purification of the blood of undesired particles.

Although the above publication offers an advantageous procedure for setting TMP, it has been seen to be possible to further improve the solution described in the above publication.

SUMMARY

In particular, an aim of the present invention is to make available an apparatus for blood treatment which is capable of determining a setting value of the TMP in a way which is simple and more rapid with respect to the typical mode in known-type procedures.

A further aim of the invention is to make available an apparatus which is able, within the limits of possibility, to increase the volume of liquid exchanged with the patient.

A further aim of the invention is to make available an apparatus which, though accelerating the TMP setting search sequence, is nonetheless able to operate in safety.

A further aim is to provide an apparatus which is able to take account of any changes in the operating conditions of some components of the apparatus itself.

At least one of the above-indicate aims is substantially attained by a treatment apparatus according to one or more of the accompanying claims or according to one or more of below aspects.

Aspects of the invention are illustrated herein below.

In a first aspect, a control method is provided for an apparatus for extracorporeal blood treatment of a type comprising: at least one treatment unit having at least one first chamber and at least one second chamber which are separated from one another by a semipermeable membrane; at least one blood removal line connected with an inlet port of the first chamber and predisposed to remove blood from a patient; at least one blood return line connected with an outlet port of the first chamber and predisposed to return treated blood to the patient; at least one infusion line of a replacement fluid; at least one fluid evacuation line connected with an outlet port of the second chamber for receiving a filtered fluid through the semipermeable membrane; a transmembrane pressure regulation device between the first and second chambers of the treatment unit, the regulation device being active on at least one of the lines; and a control unit connected with the regulation device. The control method is preferably performed by control unit and comprises a setting sequence of the transmembrane pressure which includes setting non-uniform pressure increases. In practice the control unit is configured or programme to perform the control method in accordance with the aspects described herein.

In a second aspect, in accordance with the first aspect, the setting sequence comprises the following stages:

commanding the regulating device by setting a first increase ($\delta TMP_1$) at a first value of the transmembrane pressure ($TMP_1$) in order to reach a second transmembrane pressure ($TMP_2$);

determining a value of a control parameter ($\varphi_1$) corresponding to the first increase in transmembrane pressure;

comparing the value of the control parameter ($\varphi_1$) with a reference value ($\varphi_{ref}$) and, if the value of the control parameter is greater than the reference value, commanding the regulating device by setting a second increase ($\delta TMP_2$) on the transmembrane pressure which is greater than the first increase ($\delta TMP_1$) in order to reach a third value of the transmembrane pressure ($TMP_3$).

In a third aspect, in accordance with the first or second aspect, the control parameter comprises a parameter selected from a group comprising:

a variation between the replacement flow in the infusion line at the first transmembrane pressure value ($TMP_1$) and the replacement flow in the infusion line at the second transmembrane pressure ($TMP_2$);

the variation between the ultrafiltration flow ($Q_{UF}$) across the membrane at the first transmembrane pressure value ($TMP_1$) and the ultrafiltration flow at the second transmembrane pressure value ($TMP_2$);

the replacement flow in the infusion line at the second transmembrane pressure value ($TMP_2$);

the ultrafiltration flow through the membrane at the second transmembrane pressure value ($TMP_2$).

In a fourth aspect, in accordance with any one of the aspects from the first to the third aspects, the setting sequence comprises a stage of terminating the setting sequence if the value of the control parameter is less than the reference value and then setting the second pressure value ($TMP_2$) as the setting value of the transmembrane pressure at which the regulating device is made to operate.

In a fifth aspect, in accordance with any one of the preceding aspects, the setting sequence comprises a plurality (n) of stages, with n being greater than 2. In this case the setting sequence comprises the following further stages:

determining a value of a control parameter ($\varphi_1$) corresponding to an nth transmembrane pressure increase;

comparing the value of the control parameter ($\varphi_n$) with a reference value ($\varphi_{ref(n)}$), if the value of the control parameter is greater than the respective reference value, determining an (n+1)th increase ($\delta TMP_{n+1}$) of an entity which is greater than the entity of the nth increase ($\delta TMP_n$).

In a sixth aspect, in accordance with the fifth aspect, the setting sequence comprises verifying if the nth increase was of a smaller entity than a predetermined value and, in that case, proceeding with the further stage of determining an (n+1)th increase ($\delta TMP_{n+1}$) of a greater entity than the nth increase ($\delta TMP_n$). Thereafter, the setting sequence comprises a further stage of commanding the regulating device by setting the transmembrane pressure with the (n+1)th increase ($\delta TMP_{n+1}$).

In a seventh aspect, in accordance with any one of the preceding aspects, the control method comprises sequentially repeating the setting sequence stages, in which the setting sequence is terminated when the control parameter value ($\varphi_1$, $\varphi_n$) is less than or equal to the reference value.

In an eighth aspect, in accordance with any one of the preceding aspects, the control method comprises commanding the regulating device, setting as normal working transmembrane pressure the value at which the control parameter value ($\varphi_1$, $\varphi_n$) is less than the value of the respective reference parameter.

In a ninth aspect, in accordance with any one of the preceding aspects, the control method comprises calculating the (n+1)th increase ($\delta TMP_{n+1}$) as a function of the control parameter value corresponding to the nth increase in transmembrane pressure ($\delta TMP_n$).

In a tenth aspect, in accordance with any one of the preceding aspects, the control method comprises calculating the (n+1)th increase ($\delta TMP_{n+1}$) as a function of the control parameter value ($\varphi_n$) corresponding to the nth increase ($\delta TMP_n$) and the value of the nth transmembrane pressure increase ($\delta TMP_n$).

In an eleventh aspect, in accordance with any one of the preceding aspects, the control method comprises calculating the (n+1)th increase ($\delta TMP_{n+1}$) using the following formula:

$$\delta TMP_{n+1} = (\varphi_n) \cdot (K)$$

where:
K is the relation between the value of the nth transmembrane pressure increase ($\delta TMP_n$) and the value of a correcting factor ($\varphi_c$),
$\varphi_n$ is the value of the control parameter corresponding to the nth transmembrane pressure increase ($\delta TMP_n$).

In a twelfth aspect, in accordance with any one of the preceding aspects, the control method comprises that at least two successive pressure increases are included. In particular, the method comprises calculating the second increase ($\delta TMP_2$) as a function of the control parameter value ($\varphi_1$) corresponding to the first increase ($\delta TMP_1$).

In a thirteenth aspect, in accordance with the preceding aspect, the control method comprises calculating the second increase ($\delta TMP_2$) as a function of the control parameter value ($\varphi_1$) corresponding to the first increase ($\delta TMP_1$) and the value of the first transmembrane pressure increase ($\delta TMP_1$), optionally using the formula:

$$\delta TMP_2 = (\varphi_1) \cdot (K)$$

where:
K is the relation between the value of the first transmembrane pressure increase ($\delta TMP_1$) and a correcting factor ($\varphi_c$).

In a fourteenth aspect, in accordance with any one of the aspects of the eleventh to the thirteenth, the value of the correcting factor is selected from the group comprising:
a predetermined value,
a mathematical function of the reference value ($\varphi_{ref}$),
a mathematical function of a treatment mode to which the apparatus has been set,
a mathematical function of a treatment mode to which the apparatus has been set and the reference value ($\varphi_{ref}$).

In a fifteenth aspect, in accordance with the thirteenth and the fourteenth aspect, the value of the correcting factor is greater than or equal to the reference parameter, optionally in which the reference parameter ($\varphi_{ref}$) has a predetermined value comprised between 2 and 4 ml/min, and in which the correcting factor ($\varphi_c$) has a predetermined value comprised between 3 and 5 ml/min.

In a sixteenth aspect, in accordance with any one of the preceding aspects, the control parameter comprises a parameter selected from a group comprising:
the variation between the replacement flow in the infusion line (9; 9a, 9b) at the nth transmembrane pressure value ($TMP_n$) and the replacement flow in the infusion line at the (n+1)th transmembrane pressure value ($TMP_{n+1}$);
the variation between the ultrafiltration flow ($Q_{UF}$) across the membrane (5) at the nth transmembrane pressure value ($TMP_n$) and the ultrafiltration flow at the (n+1)th transmembrane pressure ($TMP_{n+1}$);
in which the sequence comprises, in response to the command stage of the regulating device (20) for setting a transmembrane pressure increase ($\delta TMP_1$; $\delta TMP_2$; $\delta TMP_n$), a corresponding stage of varying a flow rate through the at least one infusion line in accordance with a predetermined control strategy; and in which n varies from 1 to the total number of pressure increases set during the sequence.

In a seventeenth aspect, in accordance with any one of the preceding aspects, the control method comprises verifying that each pressure increase is less than a maximum safety value, optionally in which the maximum safety value is less than or equal to 100 mmHg.

In an eighteenth aspect, in accordance with any one of the preceding aspects, the control method comprises enabling a user to enter commands via at least one user interface connected with the control unit, the control unit being configured to receive command signals relating to the commands entered by a user via the user interface.

In a nineteenth aspect, in accordance with the preceding aspect, the control method comprises: receiving, in the control unit, a start command for the sequence following a command insertable by a user acting on a manual activating element of the interface (22), and/or automatically initiating the sequence.

In a twentieth aspect, in accordance with the preceding aspect, the control method comprises:
measuring a time that has run from the start of a patient's treatment,
automatically activating a first sequence, after a first time interval ($T_1$) from the start of treatment,
measuring a time that has run from the end of the first sequence,
automatically activating a sequence, after a second time interval ($T_2$) from the end of the first sequence.

In a twenty-first aspect, in accordance with the preceding aspect, the control method comprises: activating each successive sequence, after a predetermined time interval ($T_n$) from the end of a preceding sequence.

In a twenty-second aspect, in accordance with the 19th and 20th aspects, the duration of the time intervals ($T_1$, $T_2$, $T_n$) is not uniform; optionally the duration of each time interval after the first is greater than the duration of a time interval that precedes it.

In a twenty-third aspect, in accordance with any one of the preceding aspects, the control method comprises that during the setting sequence and following each transmembrane pressure increase command, there is a time transitory ($T_r$) before effecting a subsequent transmembrane pressure increase.

In a twenty-fourth aspect, in accordance with any one of the preceding aspects, the duration of the time transitory ($T_r$) is not uniform and is optionally a function of the pressure increase between a transmembrane pressure value ($TMP_n$) and a next ($TMP_{n+1}$).

In a twenty-fifth aspect, in accordance with the preceding aspect, the control method comprises that each stage of comparison of the control parameter value ($\varphi_1$, $\varphi_n$) with a respective reference value ($\varphi_{ref}$) is effected after the time transitory ($T_r$), with the aim of enabling a stabilisation of the value of the control parameter.

In a twenty-sixth aspect, in accordance with any one of the preceding aspects, the regulating device (20) comprises at least one first pump (13) located on the evacuation line, and the method comprises that pressure increases are set by regulating a flow rate of the pump.

In a twenty-seventh aspect, in accordance with any one of the preceding aspects, the regulating device (20) comprises at least one second pump (16) located on the infusion line, the control method comprising regulating the second pump at least according to:

a set value of treatment time, a set value of weight loss and the current value of the ultrafiltration flow across the membrane; or, alternatively,
a set value of the volume of total infusion to be attained at the end of treatment and a set value for weight loss to be attained at end of treatment.

In a twenty-eighth aspect, in accordance with the preceding aspect, the regulating device (20) comprises at least one second pump (16) located on the infusion line, the control method comprising stages of:
regulating the second pump (16) at least according to a set value for total infusion volume to be attained at end of treatment and a set value for weight loss to be attained at end of treatment; and calculating an approximation of a remaining treatment time according to the remaining weight loss and a current flow value of weight loss.

In a twenty-ninth aspect, in accordance with any one of the preceding aspects, the apparatus comprises one or more pressure sensors ($S_1$, $S_2$, $S_3$, $S_4$) located on one or more lines and connected with the control unit, the pressure sensors sending pressure signals to the control unit, the control method comprising determining a current value of the transmembrane pressure from the pressure signals.

In a thirtieth aspect, in accordance with any one of the preceding aspects, the apparatus comprises at least one infusion sensor ($S_5$) selected from a group comprising a flow sensor, a mass sensor, a weight sensor, a revolution sensor of the second pump (16), the infusion sensor being active on the infusion line and connected to the control unit (15) for detecting an infusion flow through the infusion line; and/or
at least one ultrafiltration sensor ($S_6$) selected from the group comprising a flow sensor, a mass sensor, a weight sensor, the ultrafiltration sensor being active on an evacuation line and connected to the control unit (15) such as to detect an ultrafiltration flow across the membrane (5).

In a thirty-first aspect, in accordance with the 29th or the 30th aspect, the pressure sensors ($S_1$, $S_2$, $S_3$, $S_4$) comprise at least one pressure sensor ($S_2$) located on the evacuation line and at least one pressure sensor ($S_3$, $S_4$) located on the removal and/or the delivery line, the method comprising receiving, for example in the control unit, pressure signals from the pressure sensors and calculating an instant transmembrane pressure value on the basis of the pressure signals.

In a thirty-second aspect, in accordance with the 30th and 31st aspects, the control method comprises calculating the value of the control parameter on the basis of detected values of the infusion flow and/or the ultrafiltration flow.

In a thirty-third aspect in accordance with any one of the preceding aspects, the control method comprises performing, following a setting sequence, an adjustment stage (A) of the setting value to the transmembrane pressure (TMP), optionally in which following the second or third or last setting sequence there is an adjustment stage (A) comprising a reduction ($\delta TMP_{fin}$) of the setting value of the transmembrane pressure determined following the sequence.

In a thirty-fourth aspect in accordance with any one of the preceding aspects, the apparatus exhibits at least one blood pump, for example operatively connected to the control unit, operating at the removal line or the return line. The method comprises detecting a variation in the set value of the blood flow rate, verifying whether the variation is of a greater entity than a predetermined threshold, interrupting the setting sequence if the variation in the set value of the blood flow is of a greater entity than a predetermined threshold.

In a thirty-fifth aspect a control method for an apparatus for extracorporeal blood treatment is provided, comprising:

at least one treatment unit having at least one first chamber and at least one second chamber separated from one another by a semipermeable membrane;
at least one blood removal line connected to an inlet port of the first chamber and predisposed to remove blood from a patient;
at least one blood return line connected to an outlet port of the first chamber and predisposed to return treated blood to the patient;
at least one replacement fluid infusion line connected to the blood return line, upstream of the chamber;
at least one fluid evacuation line connected to an outlet portion of the second chamber for receiving at least one filtered fluid through the semipermeable membrane;
a regulating device of a transmembrane pressure between the first and the second chamber of the treatment unit, the regulating device being active on at least one of the lines; and at least one blood pump operating on the removal line or the return line.

The control method, which can for example be performed by a control unit connected to the blood pump and the regulating means, comprises stages of:
performing a setting sequence of the transmembrane pressure,
detecting a variation in the set value of the blood flow,
verifying whether the variation is of a greater entity than a predetermined threshold,
interrupting the setting sequence if the variation in the set value of the blood flow is greater than the predetermined threshold.

Further, the setting sequence can comprise the further characteristics described in one or any aspects preceding aspect no. 34.

In a thirty-sixth aspect a control method is provided for an apparatus for extracorporeal blood treatment comprising:
at least one treatment unit having at least one first chamber and at least one second chamber separated from one another by a semipermeable membrane;
at least one blood removal line connected to an inlet port of the first chamber and predisposed to remove blood from a patient;
at least one blood return line connected to an outlet port of the first chamber and predisposed to return treated blood to the patient;
at least one infusion line of a replacement fluid connected to the blood removal line, upstream of the first chamber;
at least one fluid evacuation line connected to an outlet port of the second chamber for receiving at least one filtered fluid across the semipermeable membrane;
a regulating device of a transmembrane pressure between the first and the second chamber of the treatment unit, the regulating device being active on at least one of the lines;
automatically initiating, a plurality of times during a treatment, a setting sequence of the transmembrane pressure, the stage of automatically initiating comprising:
measuring a time taken from a start of a patient's treatment, automatically activating a first sequence after a first time interval ($T_1$) from the start of the treatment,
measuring a time that has passed from an end of the first sequence, automatically activating a sequence after a second time interval ($T_2$) from the end of the first sequence, and activating each successive sequence after a predetermined time interval ($T_n$) from the end of a preceding sequence.

The control method can be performed by a control unit connected to the regulating device. Further, the setting sequence can comprise the characteristics further described in any preceding aspect before aspect no. 34.

In a thirty-seventh aspect in accordance with the preceding aspect, the duration of the time intervals ($T_1$, $T_2$, $T_n$) is not uniform. For example, the duration of each time interval ($T_2$, $T_n$) following the first is greater than the duration of a time interval preceding it.

In a thirty-eighth aspect in accordance with any of aspects from the 35th to the 37th, each setting sequence comprises the following stages:
commanding the regulating device, imposing a first increase ($\delta TMP_1$) on a first transmembrane pressure value ($TMP_1$) such as to reach a second transmembrane pressure value ($TMP_2$),
determining a value of a control parameter ($\varphi_1$) corresponding to the first transmembrane pressure increase,
comparing the value of the control parameter ($\varphi_1$) with a reference value ($\varphi_{ref}$) and, if the control parameter is greater than the reference value,
commanding the regulating device by imposing a second increase ($\delta TMP_2$) on the transmembrane pressure such as to reach a third transmembrane pressure value ($TMP_3$).

In a thirty-ninth aspect, in accordance with the preceding aspect the second increase ($\delta TMP_2$) is greater than the first increase ($\delta TMP_1$), optionally in which the second increase ($\delta TMP_2$) is calculated as a function of the control parameter value ($\varphi_1$) corresponding to the first increase ($\delta TMP_1$) and the value of the first transmembrane pressure increase ($\delta TMP_1$), and still more optionally using the formula:

$$\delta TMP_2 = (\varphi_1) \cdot (K)$$

where:
K is the relation between the value of the first transmembrane pressure increase ($\delta TMP_1$) and a correcting factor ($\varphi_c$).

In a fortieth aspect, the apparatus on which the control method of any one of the preceding aspects is applied comprises an infusion line (9, 9a) of a replacement fluid directly connected in pre-dilution with the removal line; and/or an infusion line (9b) of a replacement fluid directly connected in post-dilution with the return line. Note that optionally there can also be a second pre-dilution infusion line.

In a forty-first aspect the control unit is configured or programmed for performing the control method of any one of the preceding aspects. The control unit can be analog or digital (for example a PC with one or more processors) or a combination of analog and digital units.

In a forty-second aspect a data storage unit is provided for storing instructions which, when performed by the control unit of an apparatus for blood treatment, determine the performing of the control method on the apparatus in accordance with any one of the aspects from the first to the forty-first. For example, the data support unit can comprise a mass storage, for example optical or magnetic, an electromagnetic signal, a re-programmable memory (EPROM, FLASH) or a memory of another nature.

In a forty-third aspect, an apparatus for extracorporeal blood treatment comprises a control unit which is programmed or configured for performing a control method of any one of the aspects from the first to the forty-first.

DESCRIPTION OF THE DRAWINGS

Some drawings relating to aspects of the invention are provided by way of example.

In particular.

DETAILED DESCRIPTION

Figure 1:
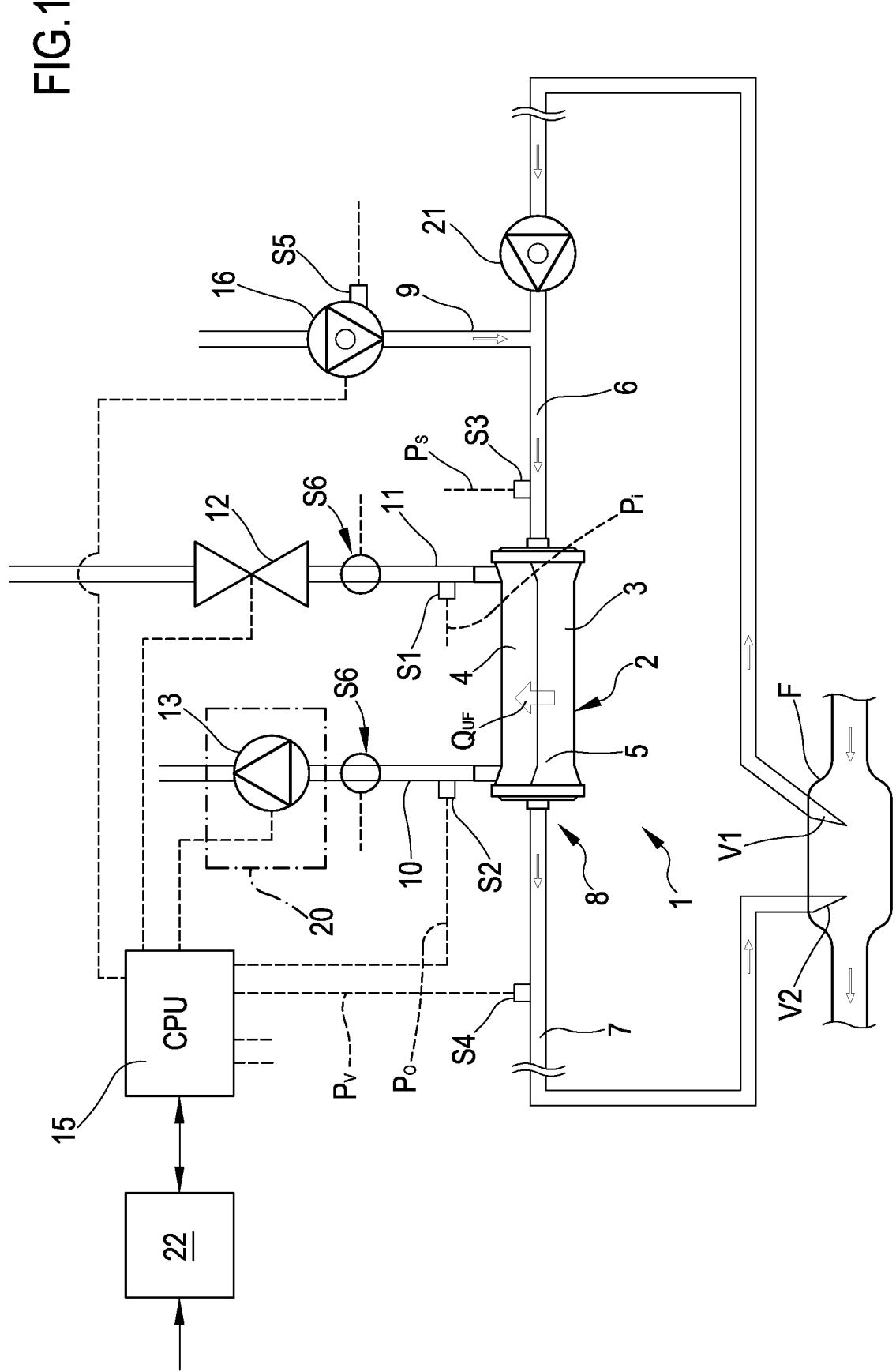
FIG. 1 is a schematic illustration of a first example of an apparatus for blood treatment according to the invention.

With reference to the accompanying figures of the drawings, 1 denotes in its entirety an apparatus for extracorporeal blood treatment. The apparatus 1 comprises at least a treatment unit 2, for example a hemofilter, a hemodiafilter, a plasma filter or an ultrafilter, having at least a first chamber and at least a second chamber 3 and 4 separated from one another by a semipermeable membrane 5.

A blood removal line 6 is connected with an inlet port of the first chamber 3 and is predisposed, in operating conditions of connection to a patient, to remove blood from a vascular access V1 inserted, for example, in a fistula F on the patient. A blood return line 7 connected with an outlet port of the first chamber is predisposed to receive the treated blood from the treatment unit and to return the treated blood to a further vascular access V2 connected to the patient's fistula. Note that the configuration of the vascular access can be of any type; for example a catheter, a port implanted in the patient, a cannula etc. In practice, the blood removal line 6, the first chamber 3 of the treatment unit and the blood return line 7 to the patient are part of an extracorporeal blood circuit 8 which, during the use of the apparatus 1, circulates the blood externally of the patient under treatment.

An infusion line 9 (see FIG. 1), or several infusion lines 9a, 9b (see FIG. 2), of a replacement fluid is/are connected to the blood removal line 6. In FIG. 1, the infusion line is connected upstream of the first chamber 3, while in FIG. 2 the line 9a is connected upstream while the line 9b is connected downstream of the unit 8; note that further infusion lines can also be comprised, for example connected downstream and/or upstream of the treatment unit.

Figure 2:
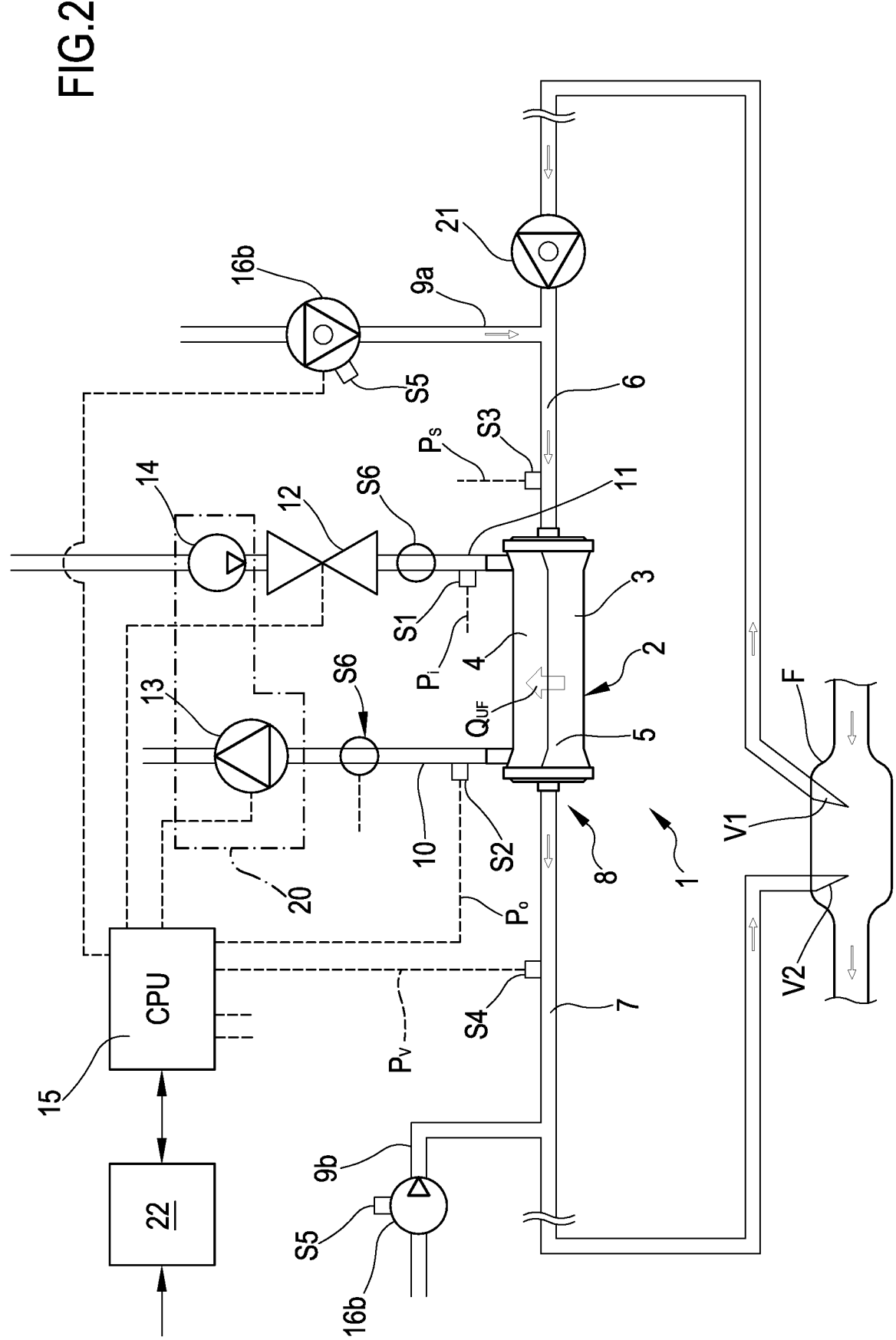
FIG. 2 is a schematic illustration of a second example of an apparatus for blood treatment, according to the invention.

The apparatus 1 further comprises at least a fluid evacuation line 10 connected to an outlet port of the second chamber 4 for receiving at least a fluid filtered across the semipermeable membrane. In the examples of FIGS. 1 and 2, there is also a supply line 11 of a fresh fluid treatment; however the presence of such a line is not strictly necessary; in the absence of the line 11, the apparatus is in any case able to perform treatments such as ultrafiltration or hemofiltration. In a case where there is the supply line 11 of a fresh fluid, a fluid check organ 12 can be used to selectively enable or disable a fluid passage through the supply line 11, according to whether there is or not to be a purification by diffusive effect internally of the treatment unit. During the treatment the fluid and undesired particles must be moved from the first chamber towards the second chamber of the treatment unit.

The movement of fluid and/or particles creates a transmembrane pressure which is defined as the mean pressure applied on the side of the first chamber towards the side of the second chamber. Estimates for the transmembrane pressure (herein below indicated in short as TMP) can be calculated in various ways. For example, the transmembrane pressure TMP can be calculated according to one of the following formulas, which may provide slightly different TM estimates.

1) In a case in which (see FIGS. 1 and 2) there are four pressure sensors of which one ($S_1$) is on the supply line 11, one (S2) on the evacuation line 10, one (S3) on the blood removal line 6 and one (S4) on the return line 7, the value of the TMP is determined by the control unit using the pressure signals coming from the sensors from S1 to S4 and using the formula:

$$TMP = \frac{Ps + Pv}{2} - \frac{Pi + Po}{2}$$

where:
Pi is the pressure detected by sensor S1
Po is the pressure detected by sensor S2
Ps is the pressure detected by sensor S3
Pv is the pressure detected by sensor S4

2) In a case where there are three pressure sensors (or in a case in which no fluid circulates in the line 11) of which one (S2) is on the evacuation line 10, one (S1) is on the supply line 11 and one (S4) is on the return line 7, the value of the TMP is determined by the control unit using the pressure signals coming from the sensors from S2 to S4, using the formula:

$$TMP = Pv - \frac{Pi + Po}{2}$$

where:
Po is the pressure detected by sensor S2
Pi is the pressure detected by sensor S1
Pv is the pressure detected by sensor S4

3) Lastly, in a case in which there are two pressure sensors of which one is on the evacuation line 10 and one on the return line 7, the value of the TMP is determined by the control unit using the pressure signals coming from sensors S2 and S4 using the formula:

$$TMP = Pv - Po$$

where:
Po is the pressure detected by sensor S2
Pv is the pressure detected by sensor S4

The apparatus 1 further comprises a regulating device 20 of a transmembrane pressure TMP; the regulating device can be active on at least one of the above-described lines. According to requirements and the configuration of the apparatus 1, the regulating device can comprise for example: a pump placed on the ultrafiltration line, or two pumps controlled differentially as two blood pumps, one located upstream and another downstream of the filtration unit, a plurality of pumps located on the lines and controlled such as to create an ultrafiltration flow across the membrane, or combinations of one or more pumps and valves, or others besides.

In the example illustrated in FIGS. 1 and 2, the device 20 comprises an ultrafiltration pump 13 operating on the evacuation line and able to recall fluid from the second chamber. In the example of FIG. 2 there is also a supply pump 14 of a treatment fluid: in this case the regulating device 20 comprises both the ultrafiltration pump and the supply pump, which are appropriately controlled differentially such as to create an ultrafiltration flow $Q_{UF}$ across the membrane.

A control unit 15, for example analog or having a microprocessor, is connected with the regulating device and configured to control the above-described pumps. In particular, the control unit operates in such a way as to control the pump or pumps 13 and 14 such that the value of TMP measured corresponds to the set value for the TMP. In other words, the control unit acts continuously or periodically on the regulating device such that, instant by instant, the TMP measured corresponds to the value set at that instant. In this way, the ultrafiltration flow $Q_{UF}$ across the membrane and thus the quantity of fluid removed from the blood present in the first chamber is a function of the set TMP.

As illustrated in the examples of FIGS. 1 and 2, an infusion pump 16, 16a, 16b can operate on each of the lines 9, 9a, 9b; note that in the case of FIG. 2 there can alternatively be provided a single infusion pump destined to generate a fluid flow through both lines 9a, 9b: in this can the infusion lines will be connected with a single delivery line and provided with special regulating means (for example valves, or pumps, or regulable choke elements) for controlling the flow through each of the infusion lines. According to the control strategy, the control unit 10 is configured to regulate the infusion pump 9 (or the pumps 9a and 9b in the case of FIG. 2) according to various parameters.

In a first example, the overall infusion flow rate through the line 9 (or the line 9a and 9b) is controlled in accordance with a set value of treatment time, of a set value of weight loss and the current value (measured by sensors of known type and therefore not described in detail) of the ultrafiltration across the membrane. In practice, for example via a user interface 22 connected to the control unit, an operator can enter a treatment time and a desired weight loss to be attained at end of treatment. These values are received by the control unit 15 which is programmed or configured for:

controlling the regulating device 20 (in the case of FIGS. 1 and 2 primarily the ultrafiltration pump 13) such as to follow the set value of the transmembrane pressure and regulating the infusion pump 9 (or pumps 9a, 9b) such as to obtain the desired weight loss in the treatment time set by the operator. In practice, following the variations of the ultrafiltration pump which tends to maintain the transmembrane pressure aligned with the set instant value, the velocity of the infusion pump (or the infusion pumps) is also varied such that the weight loss flow follows the value set by the operator.

Alternatively, in a second example, instead of the treatment time an operator can set a total infusion volume value to be reached at the end of treatment and a weight loss value to be reached at the end of treatment. As already mentioned, a user can enter these values using the user interface 22 the apparatus 1 is provided with. In this case, the control unit 15 is configured to regulate the second pump or infusion pump at least according to a set value for total infusion volume to be reached at the end of treatment; in practice the control unit is programmed to regulate the velocity of the ultrafiltration pump in order to respect the TMP set value, and also to control the velocity of the infusion pump such that the relation between infusion flow rate and weight loss remains, instant by instant, in a constant relation, such that independently of the duration of the treatment there is the certainty that the two set objects of weight loss and total infusion of replacement fluid are achieved substantially at the same time. The control unit can optionally also be programmed to calculate an approximation of a remaining treatment time according to the remaining weight loss, and for a current value of weight loss flow.

Other control strategies can be provided: in any case, following variations in the ultrafiltration flow rate of imposed by the regulating device for following the TMP value, the infusion pump can be controlled according to the ultrafiltration according to algorithms which can be set by the operator or pre-stored in the apparatus 1.

The apparatus 1 comprises at least a sensor, acting on the infusion line, connected with the control unit for detecting an infusion flow through the infusion line and/or at least a sensor acting on the evacuation line connected with the control unit for detecting an ultrafiltration flow through the evacuation line. The sensors for detecting the flow can be volumetric, mass sensors, weight sensors such as scales, pump revolution sensors or of another type still; the sensors can be predisposed to determine absolute or differential values of the amounts measured. As the type of sensors usable is not relevant and as the methods and the sensors for detecting absolute or differential flow values are known and within the ambit of an expert in the field, no further details are given thereof in the present text.

With the aim of setting the optimal transmembrane pressure and thus maximising as far as possible the convective transport across the membrane, the control unit is programmed on manual or automatic command to perform a setting sequence of the transmembrane pressure.

The setting sequence comprises the following stages:

setting the transmembrane pressure at a first value $TMP_1$, commanding the regulating device 20, for example the ultrafiltration pump, imposing a first increase $TMP_1$ to the first transmembrane pressure value $TMP_1$ in order to reach a second transmembrane pressure value $TMP_2$; this is done for example by increasing the flow rate of the ultrafiltration pump and verifying that the measured value of the TMP reaches the value $TMP_2=TMP_1+\delta TMP_1$;

waiting for a time T and then calculating a value of a control parameter $\varphi_1$ corresponding to the second transmembrane pressure value $TMP_2$; in the illustrated example, following the variation in ultrafiltration flow, the flow along one or more infusion lines is consequently varied, according to one of the control strategies outlined herein above. In the present example, the control parameter is the variation between the infusion value through the infusion line, measured or estimated at the instant preceding the increase in pressure, and the value measured or estimated following a time interval T necessary for the infusion pump to perform the transitory of acceleration in order to compensate for the transmembrane increase;

comparing the value of the control parameter $\varphi_1$ with a reference value $\varphi_{ref}$ and, if the value of the control parameter is greater (or equal, in an alternative form) to the reference value, commanding the regulating device by imposing a second increase ($\delta TMP_2$) on the transmembrane pressure which is greater than the first increase ($\delta TMP_1$) in order to reach a third transmembrane pressure value ($TMP_3$). In the illustrated example the change in infusion flow rate is compared to a reference flow rate, for example 3 ml/min and, should the variation in the infusion flow rate be greater than 3 ml/min, the ultrafiltration pump is commanded such as to impose a TMP increase which is greater than the previous one. In this way, if following the first TMP variation the corresponding variation of ultrafiltration flow rate, and consequently the infusion flow rate, are sufficiently high and therefore such as to indicate that the treatment unit is operating in a sufficiently distant zone from the plateau zone (with reference to the characteristic curve of ultrafiltration/TMP relating to the treatment unit itself), the above-described sequence considerably increases the range of the following pressure increase, thus accelerating the search for and the setting of the optimal TMP.

If on the other hand the control parameter value is lower than the reference value, the TMP setting procedure is interrupted, as will be more fully described herein below, as the unit in such a case assumes that the optimal TMP has been reached and thus it is kept as a setting value.

Figure 3:
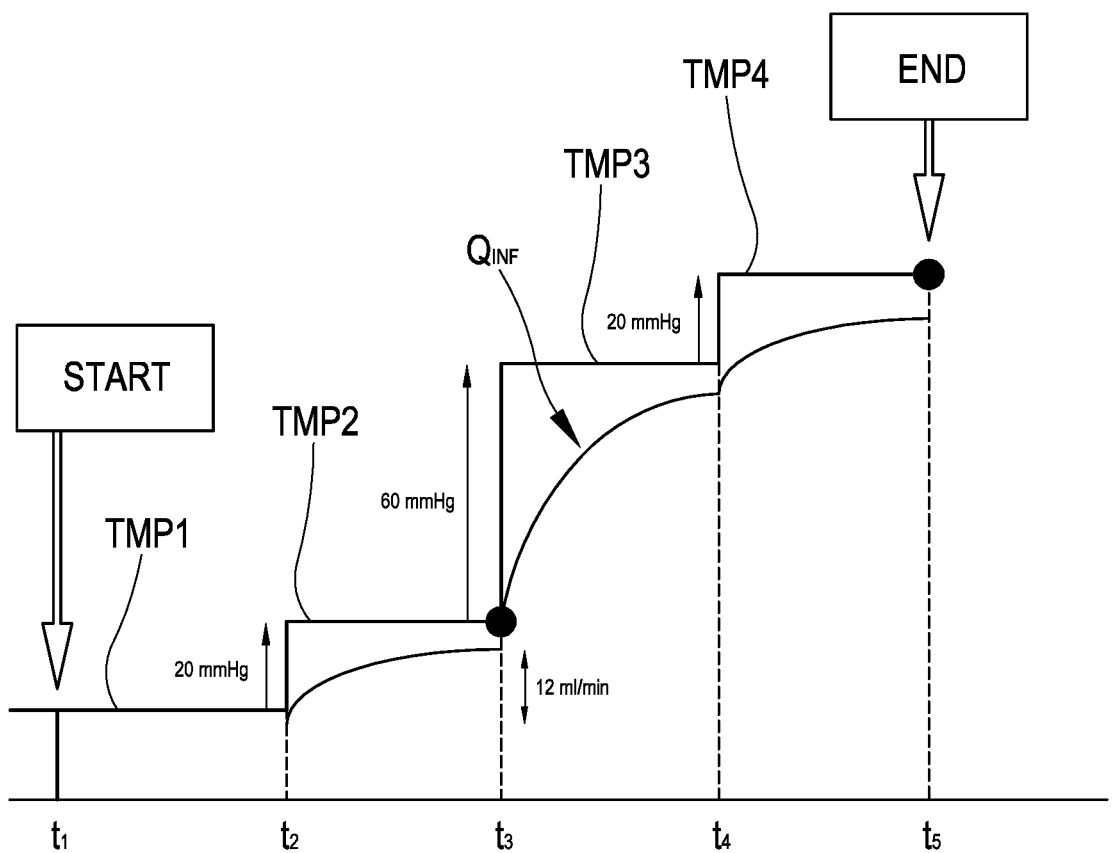
FIG. 3 is a time diagram relating to a TMP setting sequence, in an aspect of the invention.

FIG. 3 illustrates a system of Cartesian axes in which the x-axis represents the time and the ordinates the TMP pressure set instant by instant (continuous line) and the infusion flow-rate (broken line) along the line 9 (or the lines 9a and 9b): FIG. 3 also includes an embodiment of a TMP setting sequence which can be performed by a control unit which is part of an apparatus 1 of the type illustrated in FIG. 1 or FIG. 2. Following a manual command or an automatic procedure, a TMP setting sequence is initiated by the control unit. Initially ("START" in FIG. 3), the control unit maintains the TMP at a value of $TMP_1$ for a first time interval $t_1$-$t_2$. At the end of the first interval of time $t_1$-$t_2$, a pressure increase of 20 mmHg is imposed on the TMP set value, passing from the set value of TMP to a set value $TMP_2$, with a consequent activating of the ultrafiltration pump 13 and the infusion pump 16 (or at least one of pumps 16a, 16b in the case of FIG. 2). As already mentioned, the flow rate of the infusion pump 16 (or at least one of the pumps 16a, 16b in the case of FIG. 2) is schematically represented by the curve $Q_{INF}$ (broken line) in FIG. 3. As can be seen, in response to the new set TMP value, the control unit 15 also commands acceleration of the ultrafiltration pump, such as to reach the new $TMP_2$, and thus also the acceleration of the infusion pump 16 (or at least one of the pumps 16a, 16b in the case of FIG. 2), such as to balance the effect of the greater ultrafiltration, according to one of the above-described control strategies.

Still with reference to FIG. 3, in the interval $t_2$-$t_3$, the flow rate variation of the infusion pump is greater than 3 ml ($\varphi_{ref}$), for example 12 ml/min. In accordance with an aspect of the invention, the following increase in the set value of TMP is set at greater than 20 mmHg, and in the illustrated example, at 60 mmHg. In response to the new set value of TMP ($TMP_3$), the control unit also commands the acceleration of the infusion pump such as to balance the effect of the greater ultrafiltration, according to one of the above-described control strategies: as can be seen in the broken line the infusion flow rate $Q_{INF}$ is increased in the interval $t_3$-$t_4$. Note also that the duration of the interval $t_3$-$t_4$ is not necessarily equal to that of interval $t_2$-$t_3$: for example, the unit 15 can be configured such as to impose a variable interval, as great as the immediately-preceding increase in TMP, with the aim of enabling a catch-up transitory for the ultrafiltration pump and the infusion pump or pumps.

Figure 4:
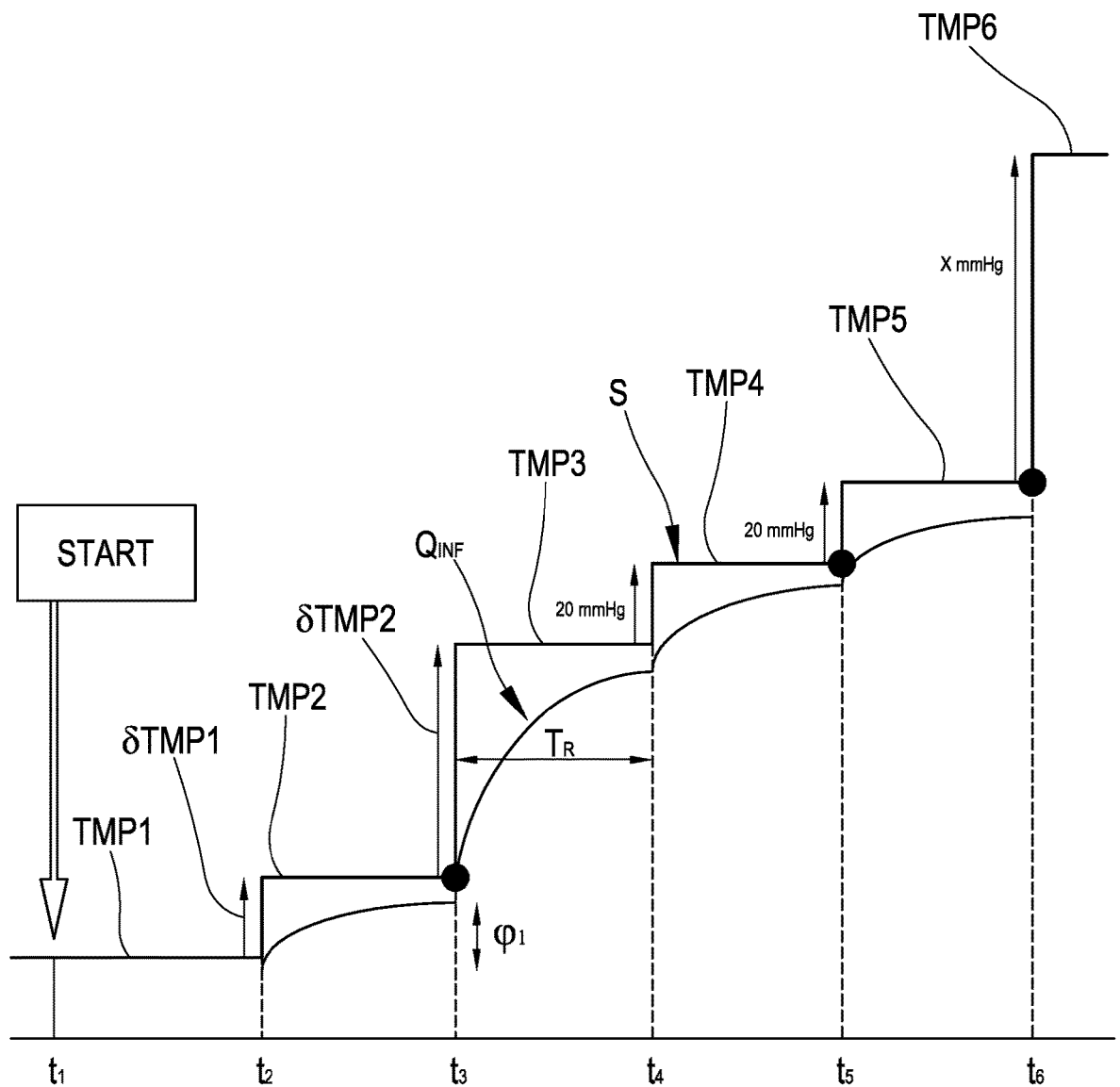
FIG. 4 is a time diagram relating to a further TMP setting sequence, in an aspect of the invention.

Still with reference to FIG. 3, at instant $t_4$ a new TMP increase of 20 mmHg is imposed, and after a further interval T (in FIG. 4: $t_4$-$t_5$), the increase in the infusion rate $Q_{INF}$ is verified. If, as in the illustrated case, the flow-rate $Q_{INF}$ varies by a value of less than 3 ml/minuto, the setting sequence is considered to be concluded ("END" in FIG. 3) and the final value of TMP to have been reached (i.e. $TMP_4$ in FIG. 3) and set as setting value. Otherwise, a new TMP increase is imposed, which can again be 20 mmHg or can be a value which is a function of the variation measured in infusion flow $Q_{INF}$.

Alternatively to what has been described, the control unit 15 can measure the variation of the ultrafiltration flow rate through a TMP leap and use the variation as a control parameter. FIG. 4 illustrates a situation in which the above-described stages are repeated up to reaching pressure $TMP_3$; thereafter, the setting sequence can comprise the variation in TMP according to one or more predetermined steps with the aim of enabling stabilisation of the control system. This or these predetermined variations of TMP are maintained smaller than or equal to a relatively low level, for example 20 mmHg. For example, FIG. 4 illustrates a small stabilising step denoted by S. After a further time interval $t_4$-$t_5$, the sequence repeats the previously-described stages with reference to intervals from $t_2$ to $t_4$. In other words, at instant $t_5$ a pressure increase of 20 mmHg is imposed on the TMP value passing to a set value $TMP_5$ with a consequent activating of the ultrafiltration pump 13 and the infusion pump 16 (or at least one of the pumps 16a, 16b in the case of FIG. 2). As can be seen, in response to the new set value of TMP, the control unit 15 also commands the acceleration of the infusion pump 16 (or at least one of the pumps 16a, 16b in the case of FIG. 2) such as to balance the effect of the greater ultrafiltration, according to one of the above-described control strategies.

If, as in FIG. 4, in the interval $t_5$-$t_6$ the flow rate variation of the infusion pump is greater than 3 ml/min, for example 12 ml/min, the subsequent increase in TMP set value is imposed at greater than 20 mmHg and, in the illustrated example, 60 mmHg. In response to the new set value of TMP ($TMP_6$), the control unit also commands the acceleration of the infusion pump such as to balance the effect of the greater ultrafiltration, according to one of the above-described control strategies. Thus, a new increase in TMP of 20 mmHg is imposed, and after a further interval T, the increase in the infusion flow rate $Q_{INF}$ will be verified. If, in response, the flow rate $Q_{INF}$ varies by a value of lower than 3 ml/minute, the setting sequence is considered to be concluded. Otherwise, the described process is newly initiated.

In general, the sequence comprises that at the start of the procedure a TMP increase is imposed which is at a predetermined value, which can be the same or can vary during the treatment, but which is known a priori and normally is relatively small, for example 20 mmHg. Increases following the first ($\delta TMP_{n+1}$) are either stabilising increases, as described above, or TMP variations calculated in accordance with the value of a control parameter ($\varphi_n$), measured or estimated, corresponding to the immediately-preceding transmembrane pressure leap ($\delta TMP_n$). The preceding stages are repeated until following a pressure step the control parameter does not satisfy the sequence terminating condition: at this point, the control unit is configured to command the regulating device 20, setting as a working transmembrane pressure the last pressure at which the control parameter value was less than the value of the respective reference parameter.

Note that in general once an increase in TMP has been performed, the control parameter used to evaluate if it is necessary or not to perform a further TMP leap of a greater entity can be any of the following:

a) the difference between the replacement flow in the infusion line, determined (measured for example using flowmeters or estimated for example on the basis of revolutions per minute of the infusion pump or pumps) at the transmembrane pressure preceding the TMP leap that has just occurred, and the replacement flow in the infusion line, determined at the transmembrane pressure subsequent to the pressure increase once the transitory has concluded;

b) the difference between the ultrafiltration flow, determined (also measured using appropriate sensors or estimated on the basis of the number of revolutions of the various pumps involved) at the transmembrane pressure preceding the TMP leap that has just occurred, and the ultrafiltration flow, determined at the transmembrane pressure after the pressure increase once the transitory has concluded;

c) the replacement flow value (measured or estimated) in the infusion line at the transmembrane pressure following the pressure increase once the transitory has concluded;

d) the ultrafiltration flow value (measured or estimated) across the membrane at the transmembrane pressure following the pressure increase once the transitory has concluded.

Passing into greater detail as regards the calculation of the TMP, the control unit is configured (in the hypothesis in which $\varphi_1 > \varphi_{ref}$) to calculate the second increase ($\delta TMP_2$) as a function of the value of the control parameter corresponding to the first increase ($\delta TMP_1$) for example as a linear function of the control parameter value ($\varphi_1$) corresponding to the first increase ($\delta TMP_1$) using the formula:

$$\delta TMP_2 = (\varphi_1) \cdot (K)$$

where:
K is the relation between the value of the first transmembrane pressure increase $\delta TMP_1$ and a correcting factor $\varphi_c$, $\varphi_1$ is the value of the control parameter (for example, the variation in the flow rate of the infusion pump) corresponding to the first transmembrane pressure increase $\delta TMP_1$.

The value of $\delta TMP_1$ is predetermined and can be comprised between 10 and 30 mmHg (for example 20 mmHg).

The value of the correcting factor can be determined in various ways; for example, the value of the correcting factor can be fixed and be greater than or equal to (preferably greater than) the reference parameter: not by way of limitation, the reference parameter $\varphi_{ref}$ can have a predetermined value comprised for example between 2 and 4 ml/min, and the correcting factor value a predetermined value comprised for example between 3 and 5 ml/min. In a second example, the value of the control parameter can be calculated as a function of the reference parameter value: $\varphi_c = f(\varphi_{ref})$. In a case in which the control parameter is the infusion flow variation, the control parameter value can be expressed by the function $\varphi_{ref}+1$. In this way, if following a first pressure increase of 20 mmHg a control parameter value were measured at 12 ml/min, and if $\varphi_{ref}=3$ ml/min, the value of the second pressure increase would be given by the formula:

$$\delta TMP_2 = (12\ ml/min) \cdot (20\ mmHg/4\ ml/min) = 60\ mmHg$$

It is also noteworthy that the reference parameter values and the correcting factor can be a function of the operating configuration of the apparatus 1. In other words, the control unit can be configured to enable the user a selection between a plurality of treatment modes, for example hemodialysis, hemofiltration in predilution, hemofiltration in post-dilution, hemofiltration in pre- and in post-dilution, hemodiafiltration in predilution, hemodiafiltration in post-dilution, hemodiafiltration in pre- and in post-dilution.

Once the treatment mode has been chosen, the control unit detects the selection and assigns a different value to the reference parameter and the correcting factor in accordance with the treatment mode selected. For example:

$$\varphi_{ref} = f_1(\text{selected treatment mode})$$

$$\varphi_c = f_2(\varphi_{ref}) + f_3(\text{selected treatment mode})$$

where $f_1$, $f_2$, $f_3$ are three functions, for example stored in a memory associated to the control unit 15.

To avoid excessive pressure leaps, the control unit is configured such as to verify that each pressure increase is less than a maximum safety value, for example 100 mmHg. The maximum safety value can be programmable by the user or automatically set by the control unit. In the latter case the control unit can also be programmed to set a different maximum safety value according to the type of treatment unit installed on the apparatus 1.

As mentioned, the described sequence can be manually activatable or can be automatically activated. For example, the apparatus 1 can comprise at least a user interface 22, connected to the control unit and having at least a manual activating element of the sequence. For example, if the interface is of the type having a touch screen, the activating element can comprise a special area of the screen on which the user can act by pressure to initiate the TMP setting sequence. The control unit is programmed to receive a start command of the sequence following the action exerted on the manual activating element. It is also possible to deactivate the sequence manually by acting on the screen or on another element of the user interface 22.

Alternatively, or additionally, the control unit 15 is programmed to initiate the setting sequence automatically. In this case the control unit 15 is programmed to measure a time between a start treatment of a patient, automatically activate a first sequence after a first time interval from the treatment start, measure a time from the end of the first sequence, and automatically activate a second sequence after a second time interval from the end of the first sequence. In the example of FIG. 4, a first setting sequence is activated after a time interval $T_1$ from the start of treatment, a second setting sequence is activated after a time interval $T_2$ from the end of the first sequence, and finally a third sequence is activated after a time interval $T_3$ from the end of the second sequence. According to the type of requirement, such as for example the duration of treatment, type of treatment unit and more besides, a different number (two, three or more) of sequences can be comprised during the course of the treatment.

The duration of the time intervals between consecutive sequences is optionally not uniform: for example the duration of each time interval following the first ($T_2$, $T_3$, . . . $T_n$) is greater than the duration of a time interval preceding it.

Figure 5:
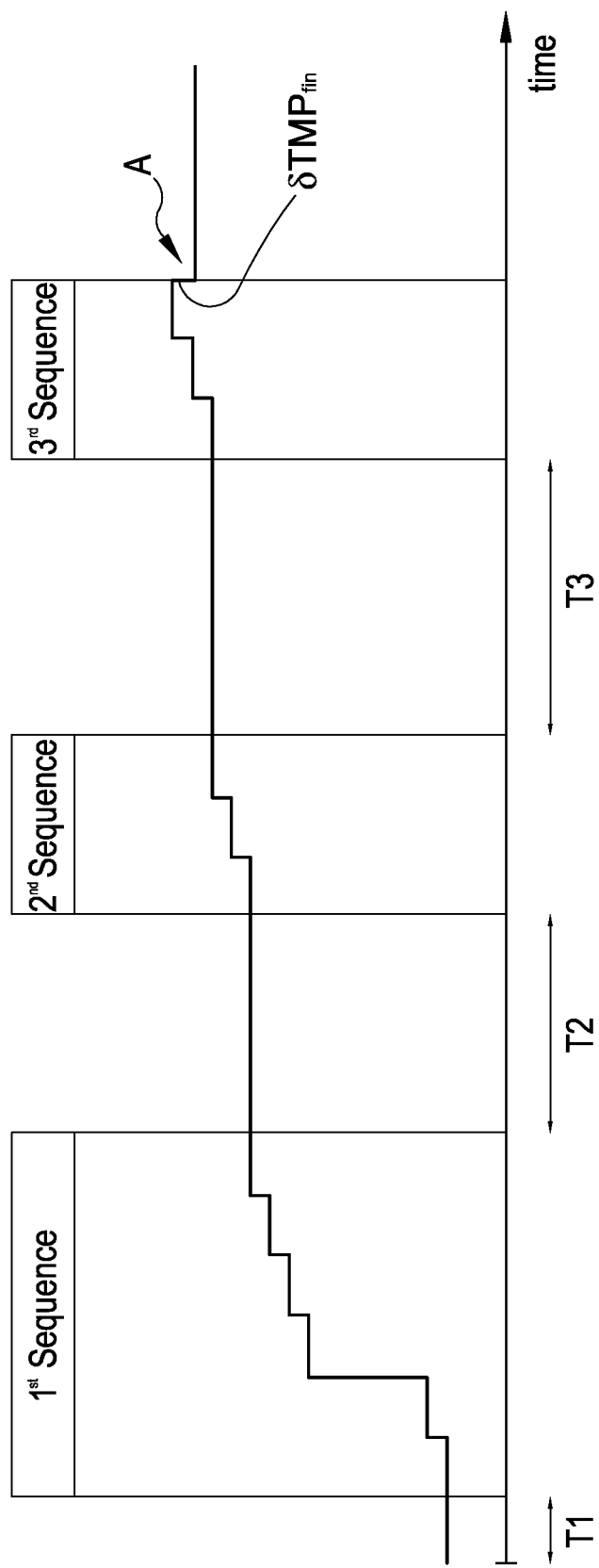
FIG. 5 is a time diagram relating to a plurality of successive sequences of TMP settings, according to an aspect of the invention.

As shown in FIG. 5, the control unit 15 can also be programmed to effect, following a first setting sequence, a stage of adjusting the TMP setting value. In particular, following the second or third or last setting sequence, a stage of adjustment is provided (denoted by A in FIG. 5) comprising lowering the TMP value, determined by a setting sequence of a predetermined value $\delta TMP$ with the aim of preventing reaching the plateau zone of the TMP/UF curve. FIG. 5 shows a succession of three setting sequences in which, following the third and final sequence, a reduction of the TMP is made by a $\delta TMP$ value, for example 20 mmHg.

Figure 6:
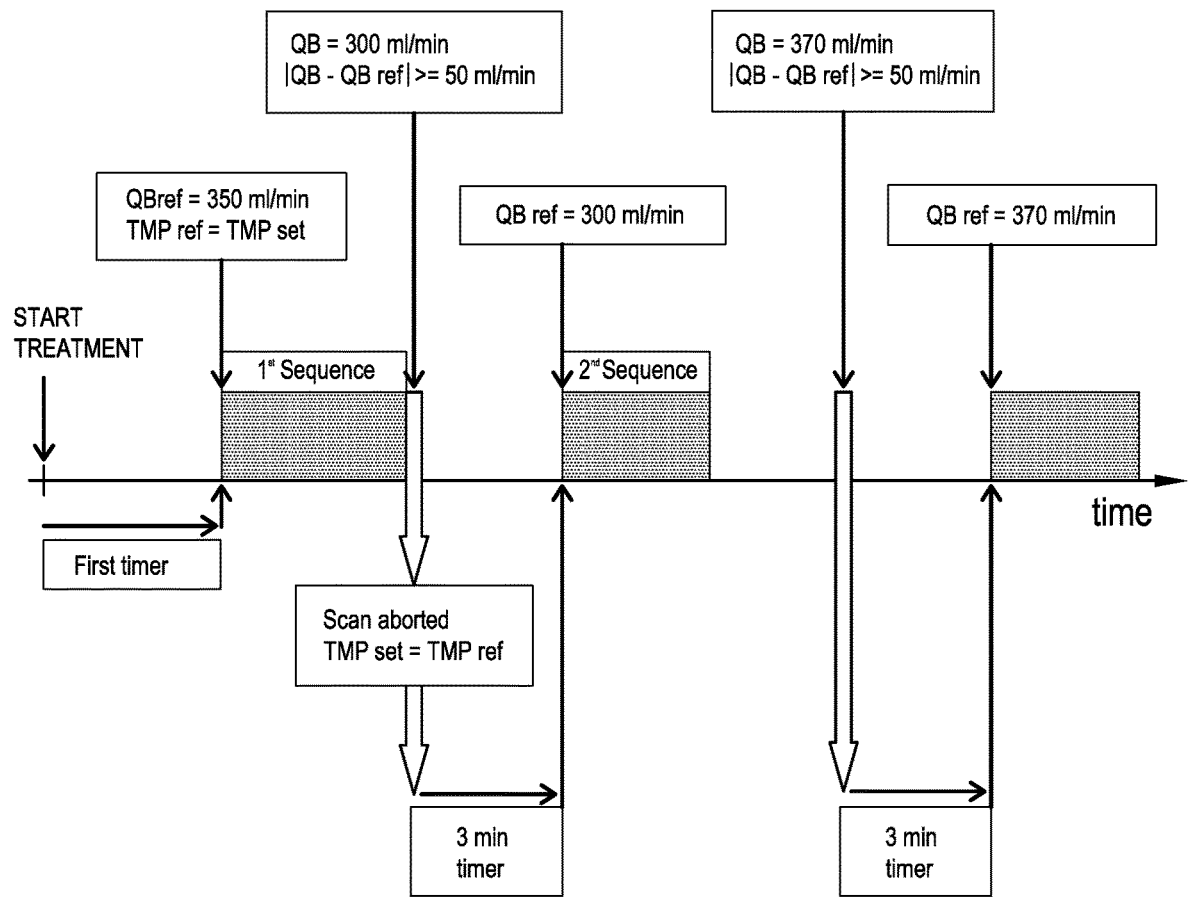
FIG. 6 is a time diagram relating to a plurality of TMP setting sequences, in the presence of variations in the blood flow rate setting.

As can be seen in FIGS. 1 and 2, the apparatus 1 comprises at least a blood pump 21 operatively connected with the control unit 15 and operating at the removal line 6 or the return line 7. From the constructional point of view, the blood pump can be a peristaltic pump. As shown in FIG. 6, the control unit 15 can also be programmed to detect a variation in the set value of the blood flow, which for example can be altered via the user interface 22. Normally the flow rate value is set at the start of treatment and kept constant during the treatment. If, however, the blood flow rate changes, the control unit 15 can be programmed to:
- detect the change,
- verify whether the change is greater than a predetermined threshold,
- interrupt the setting sequence (whether manually or automatically initiated).

For example, the control unit 15 interrupts the sequence if a variation is detected which is greater for example than 50 ml/min (see block "Scan aborted $TMP_{set}=TMP_{ref}$" in FIG. 6 during the first sequence): this is because the variation in the blood flow rate leads to a TMP variation.

If the blood flow rate drops during the setting sequence, for example if the blood rate is reduced by a quantity equal or above 50 ml/min, the control unit can be programmed to:
- interrupt the set sequence (refer again to FIG. 6 and to the interruption of the first sequence),
- set a new TMP starting value from which to start a new setting sequence, whether the new sequence starts automatically or starts with a manual on/off command,
- in a case where an automatic procedure is set, automatically start the sequence after a minimum time (for example 3 minutes) from the setting of a new blood flow rate;
- In a case where a manual procedure is set, send a user message to the user interface 22 which invites the user to initiate the sequence after a minimum time from the imposing of a new blood flow rate.

If the blood flow rate is reduced in an interval between two consecutive setting sequences (see in FIG. 6 the setting of the flow rate at 370 ml/min), the control unit can be programmed to:
- set a new TMP start value from which to initiate a new setting sequence, whether the new sequence initiates automatically or by manual on/off switching;
- in a case where an automatic procedure is set, automatically initiate the sequence after the minimum times (for example 3 minutes) from the setting of the new blood flow rate;
- if a manual procedure is set, send the user interface 22 a user message inviting the user to initiate the sequence after a minimum time from the imposing of a new blood flow rate.

If the blood flow rate is increased during the performing of the setting sequence, for example if the blood flow rate is increased by more than 50 ml/min, the control unit 15 can be programmed to:
- interrupt the setting sequence,
- set a new TMP start value from which to initiate a new setting sequence, whether the new sequence initiates automatically or by manual on/off switching; if an increase in TMP has already been made with respect to a start-treatment value, the new TMP value is the one obtained by reducing the currently-set TMP by a predetermined step, for example 20 mmHg,
- in a case where an automatic procedure is set, automatically initiate the sequence after the minimum time (for example 3 minutes) from the setting of the new blood flow rate;
- if a manual procedure is set, send the user interface 22 a user message inviting the user to initiate the sequence after a minimum time from the imposing of a new blood flow rate.

If the blood flow rate is increased during an interval between two setting sequences, for example if the blood flow rate is increased by more than 50 ml/min, the control unit 15 can be programmed to:
- in a case where an automatic procedure is set, automatically initiate the sequence after a minimum time (for example 3 minutes) from the setting of the new blood flow rate;
- if a manual procedure is set, send the user interface 22 a user message inviting the user to initiate the sequence after a minimum time from the imposing of a new blood flow rate.

The invention claimed is:

1. A process of setting transmembrane pressure between a first chamber and a second chamber of a treatment unit in an apparatus for extracorporeal blood treatment,
the apparatus comprising:
- at least one blood removal line connected with an inlet port of the first chamber and predisposed to remove blood from a patient;
- at least one blood return line connected to an outlet port of the first chamber and predisposed to return treated blood to the patient;
- at least one infusion line for providing replacement fluid, the at least one infusion line connected to one of said at least one blood removal line and said at least one blood return line; and
- at least one fluid evacuation line connected to an outlet port of the second chamber configured to receive at least one fluid filtered across the semipermeable membrane;

the treatment unit having the first chamber and the second chamber separated from one another by a semipermeable membrane, wherein a difference in pressures in the first chamber and the second chamber across the semipermeable membrane defines a transmembrane pressure;

the process comprising a setting sequence that comprises:
- imposing a first increase in transmembrane pressure ($\delta TMP_1$) on a first transmembrane pressure ($TMP_1$) to reach a second transmembrane pressure ($TMP_2$);
- determining a value of a control parameter ($\varphi_1$) corresponding to the first increase in transmembrane pressure, wherein the control parameter is related to a variation between a replacement flow in the at least one infusion line at the first transmembrane pressure ($TMP_1$) and a replacement flow in the at least one infusion line at the second transmembrane pressure ($TMP_2$);
- comparing the value of the control parameter ($\varphi_1$) corresponding to the first increase in transmembrane pressure ($\delta TMP_1$) with a reference value ($\varphi_{ref}$);
- determining if the value of the control parameter ($\varphi_1$) corresponding to the first increase in transmembrane pressure ($\delta TMP_1$) is greater than the reference value ($\varphi_{ref}$); and
- if the value of the control parameter ($\varphi_1$) corresponding to the first increase in transmembrane pressure ($\delta TMP_1$) is greater than the reference value ($\varphi_{ref}$), imposing a second increase ($\delta TMP_2$) on the transmembrane pressure which is greater than the first increase in transmembrane pressure ($\delta TMP_1$) to reach a third transmembrane pressure ($TMP_3$).

2. The process of claim 1, wherein imposing a second increase ($\delta TMP_2$) on the transmembrane pressure comprises terminating the setting sequence if the value of the control parameter ($\varphi_1$) corresponding to the first increase in transmembrane pressure is not greater than the reference value ($q_{ref}$).

3. The process of claim 1 wherein imposing a second increase ($\delta TMP_2$) on the transmembrane pressure comprises imposing the second transmembrane pressure ($TMP_2$) as a setting value of the transmembrane pressure if the value of the control parameter ($\varphi_1$) corresponding to the first increase in transmembrane pressure is not greater than the reference value ($\varphi_{ref}$).

4. The process of claim 1, comprising repeating execution of the process.

5. The process of claim 4, comprising adopting the third transmembrane pressure ($TMP_3$) of a preceding execution of the process as the first transmembrane pressure ($TMP_1$) when repeating execution of the process.

6. The process of claim 1, wherein the second increase ($\delta TMP_2$) is calculated as a function of the value of the control parameter ($\varphi_1$) corresponding to the first increase in transmembrane pressure.

7. The process of claim 1, comprising verifying that each increase in transmembrane pressure is lower than a maximum safety value.

8. The process of claim 1, wherein the apparatus comprises at least one user interface and a control unit configured to receive command signals entered by a user via the at least one user interface, wherein the process comprises:
   acting on a manual activating element of the at least one user interface to enter a start command; and
   executing the process in response to said start command.

9. The process of claim 1, wherein the process comprises:
   measuring a time that has passed from a start of treatment using the apparatus,
   executing the process after a first time interval from the start of treatment;
   measuring a time that has passed from an end of a first execution of the process;
   executing the process after a second time interval from an end of the first execution of the process; and
   activating each subsequent execution of the process after a predetermined time interval from an end of a preceding execution of the process;
   wherein the duration of the first time interval, the second time interval, and the predetermined time interval is not uniform.

10. The process of claim 1, wherein the control parameter is one of:
    a difference between a replacement flow in the at least one infusion line at the first transmembrane pressure (TMP1) and a replacement flow in the at least one infusion line at the second transmembrane pressure (TMP2); and
    a ratio between a replacement flow in the at least one infusion line at the first transmembrane pressure (TMP1) and a replacement flow in the at least one infusion line at the second transmembrane pressure (TMP2).

11. A process of setting transmembrane pressure between a first chamber and a second chamber of a treatment unit in an apparatus for extracorporeal blood treatment,
    the apparatus comprising:
        at least one blood removal line connected with an inlet port of the first chamber and predisposed to remove blood from a patient;
        at least one blood return line connected to an outlet port of the first chamber and predisposed to return treated blood to the patient;
        at least one infusion line for providing replacement fluid, the at least one infusion line connected to one of said at least one blood removal line and said at least one blood return line; and
        at least one fluid evacuation line connected to an outlet port of the second chamber configured to receive at least one fluid filtered across the semipermeable membrane;
    the treatment unit having the first chamber and the second chamber separated from one another by a semipermeable membrane, wherein a difference in pressures in the first chamber and the second chamber across the semipermeable membrane defines a transmembrane pressure;
    the process comprising a setting sequence that comprises:
        imposing a first increase in transmembrane pressure ($\delta TMP_1$) on a first transmembrane pressure ($TMP_1$) to reach a second transmembrane pressure ($TMP_2$);
        determining a value of a control parameter ($\varphi_1$) corresponding to the first increase in transmembrane pressure ($\delta TMP_1$), wherein the control parameter is related to a variation between the ultrafiltration flow ($Q_{UF}$) across the membrane at the first transmembrane pressure ($TMP_1$) and the ultrafiltration flow across the membrane at the second transmembrane pressure ($TMP_2$);
        comparing the value of the control parameter ($\varphi_1$) corresponding to the first increase in transmembrane pressure ($\delta TMP_1$) with a reference value ($\varphi_{ref}$);
        determining if the value of the control parameter ($\varphi_1$) corresponding to the first increase in transmembrane ($\delta TMP_1$) pressure is greater than the reference value ($\varphi$ref), and
        if the value of the control parameter ($\varphi_1$) corresponding to the first increase in transmembrane pressure ($\delta TMP_1$) is greater than the reference value ($\varphi_{ref}$), imposing a second increase ($\delta TMP_2$) on the transmembrane pressure which is greater than the first increase ($\delta TMP_1$) to reach a third transmembrane pressure ($TMP_3$).

12. The process of claim 11, wherein imposing a second increase ($\delta TMP_2$) on the transmembrane pressure comprises terminating the setting sequence if the value of the control parameter ($\varphi_1$) corresponding to the first increase in transmembrane pressure is not greater than the reference value ($\varphi_{ref}$).

13. The process of claim 11, wherein imposing a second increase ($\delta TMP_2$) on the transmembrane pressure comprises imposing the second transmembrane pressure ($TMP_2$) as a setting value of the transmembrane pressure if the value of the control parameter ($\varphi_1$) corresponding to the first increase in transmembrane pressure is not greater than the reference value ($\varphi_{ref}$).

14. The process of claim 11, comprising repeating execution of the process.

15. The process of claim 14, comprising adopting the third transmembrane pressure ($TMP_3$) of a preceding execution of the process as the first transmembrane pressure ($TMP_1$) when repeating execution of the process.

16. The process of claim 11, comprising calculating the second increase ($\delta TMP_2$) as a function of the value of the control parameter ($\varphi_1$) corresponding to the first increase in transmembrane pressure.

17. The process of claim 11, comprising verifying that each increase in transmembrane pressure is lower than a maximum safety value.

18. The process of claim 11, wherein the apparatus comprises at least one user interface and a control unit configured to receive command signals entered by a user via the at least one user interface, wherein the process comprises:
  acting on a manual activating element of the at least one user interface to enter a start command; and
  executing the process in response to said start command.

19. The process of claim 11, wherein the process comprises:
  measuring a time that has passed from a start of treatment using the apparatus,
  executing the process after a first time interval from the start of treatment;
  measuring a time that has passed from an end of the first execution of the process;
  executing the process after a second time interval from an end of the first execution of the process; and
  activating each subsequent execution of the process after a predetermined time interval from an end of a preceding execution of the process;
  wherein the duration of the first time interval, the second time interval, and the predetermined time interval is not uniform.

20. The process of claim 11, wherein the control parameter is one of:
  a difference between ultrafiltration flow ($Q_{UF}$) across the semipermeable membrane at the first transmembrane pressure ($TMP_1$) and ultrafiltration flow across the semipermeable membrane at the second transmembrane pressure ($TMP_2$); and
  a ratio between ultrafiltration flow ($Q_{UF}$) across the semipermeable membrane at the first transmembrane pressure ($TMP_1$) and ultrafiltration flow across the semipermeable membrane at the second transmembrane pressure ($TMP_2$).

* * * * *